(12) United States Patent
Bird

(10) Patent No.: US 9,788,991 B2
(45) Date of Patent: Oct. 17, 2017

(54) OSTOMY BAGS

(76) Inventor: Paul Bird, Crawley (GB)

( * ) Notice: Subject to any disclaimer, the term of this patent is extended or adjusted under 35 U.S.C. 154(b) by 42 days.

(21) Appl. No.: 13/979,787

(22) PCT Filed: Jan. 13, 2012

(86) PCT No.: PCT/GB2012/000032
§ 371 (c)(1),
(2), (4) Date: Oct. 30, 2013

(87) PCT Pub. No.: WO2012/095637
PCT Pub. Date: Jul. 19, 2012

(65) Prior Publication Data
US 2014/0046283 A1 Feb. 13, 2014

(30) Foreign Application Priority Data

Jan. 14, 2011 (GB) .................................. 1100610.3

(51) Int. Cl.
A61F 5/441 (2006.01)

(52) U.S. Cl.
CPC ...... *A61F 5/441* (2013.01); *A61F 2005/4415* (2013.01)

(58) Field of Classification Search
USPC ........................................................ 604/333
See application file for complete search history.

(56) References Cited

U.S. PATENT DOCUMENTS

| | | | | |
|---|---|---|---|---|
| 4,449,970 A | * | 5/1984 | Bevan | A61F 5/441 55/385.4 |
| 4,490,145 A | * | 12/1984 | Campbell | A61F 5/441 604/333 |
| 4,723,951 A | * | 2/1988 | Steer | A61F 5/441 55/505 |
| 4,938,750 A | * | 7/1990 | Leise, Jr. | A61F 5/441 55/385.4 |
| 5,085,652 A | * | 2/1992 | Johnsen | A61F 5/441 604/333 |
| 5,167,650 A | * | 12/1992 | Johnsen | A61B 17/32053 604/332 |
| 5,690,622 A | * | 11/1997 | Smith | A61F 5/441 128/DIG. 24 |
| 5,840,073 A | * | 11/1998 | Olsen | A61F 5/441 604/333 |
| 5,865,819 A | * | 2/1999 | Cisko, Jr. | A61F 5/445 604/327 |
| 6,015,399 A | | 1/2000 | Mracna et al. | |

(Continued)

FOREIGN PATENT DOCUMENTS

| | | |
|---|---|---|
| EP | 0985390 A1 | 3/2000 |
| GB | 2259255 A | 3/1993 |

(Continued)

OTHER PUBLICATIONS

International Search Report for PCT/GB2012/000032 mailed Jul. 5, 2012.

*Primary Examiner* — Todd J Scherbel
*Assistant Examiner* — Guy K Townsend
(74) *Attorney, Agent, or Firm* — Foley Hoag LLP

(57) ABSTRACT

An ostomy bag including in an accessible wall 1 a closable exit aperture 5 and means 4 for selectively releasing accumulated gas through the aperture 5.

4 Claims, 2 Drawing Sheets

(56) References Cited

U.S. PATENT DOCUMENTS

Figure 1:
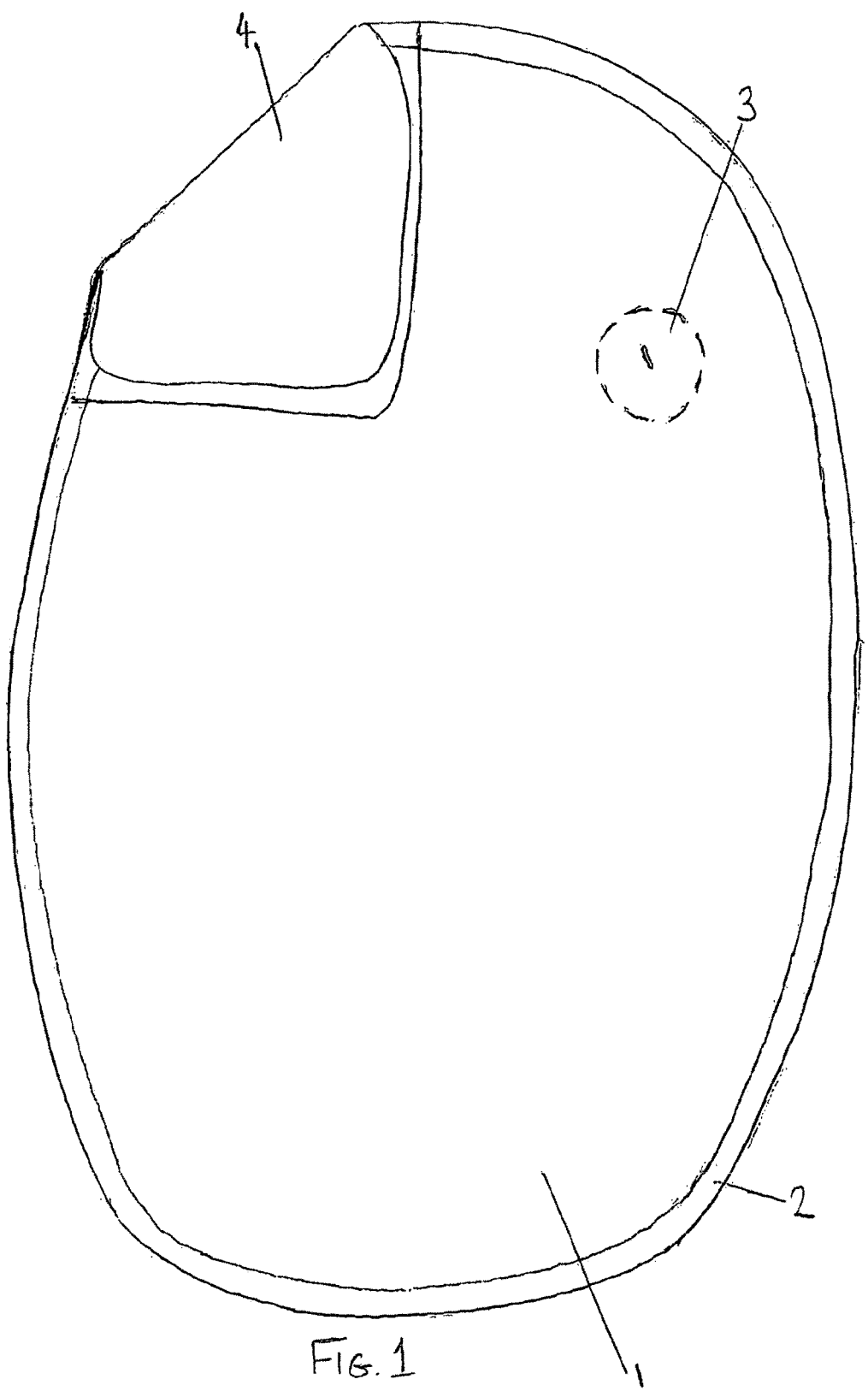

| | | | | |
|---|---|---|---|---|
| 6,709,421 B1* | 3/2004 | Falconer | ............... | A61F 5/441 |
| | | | | 604/335 |
| 8,377,020 B1* | 2/2013 | Berven | ............... | A61F 5/445 |
| | | | | 604/264 |
| 2004/0143230 A1* | 7/2004 | Hansen | ............... | A61F 5/441 |
| | | | | 604/333 |
| 2005/0240163 A1* | 10/2005 | Andersen | ............. | A61F 5/4404 |
| | | | | 604/332 |
| 2010/0152686 A1* | 6/2010 | Ryder | ................. | A61F 5/445 |
| | | | | 604/332 |
| 2014/0046283 A1* | 2/2014 | Bird | ..................... | A61F 5/441 |
| | | | | 604/333 |

FOREIGN PATENT DOCUMENTS

| | | | | |
|---|---|---|---|---|
| GB | 2371487 | * | 7/2002 | ............. A61F 5/445 |
| GB | 2371487 A | | 7/2002 | |
| WO | WO-03/065945 A1 | | 8/2003 | |

* cited by examiner

OSTOMY BAGS

This application is a 371 U.S. national stage of PCT/GB2012/000032, filed Jan. 13, 2012, which claims priority to Great Britain Application No. 1100610.3, filed Jan. 14, 2011. The entire contents of each of these applications are hereby incorporated by reference.

The present invention is directed to addressing the problem of ballooning in ostomy bags and can conveniently be introduced into any of a wide variety of ostomy bag designs.

Ballooning of a bag arises when there is an accumulation of waste gases in a partly used bag. The gases cause expansion of the bag rendering it quite solid to the touch and uncomfortable to wear. It is not always convenient for a wearer to disrobe and detach or empty the bag to address this problem. Some gas can be released through a filter provided in the bag but the speed of gaseous release provided by the filter is often not fast enough to provide timely relief to the user.

The present invention provides a convenient solution to the problem of ballooning.

In accordance with the present invention there is provided an ostomy bag including in an accessible wall a closable exit aperture and means for selectively releasing accumulated gas through the aperture.

The exit aperture can conveniently be resealably opened by a closure which covers the aperture and attaches to the bag by means of a peelable adhesive. The closure may conveniently be provided in the form of a sealing flap which folds down from a seam around the edge of the bag. Alternatively, the closure may comprise a patch which can be completely detached from the bag and optionally replaced with another. Alternative resealable means to a peelable adhesive will no doubt occur to the skilled addressee and include, without limitation, a mechanical seal comprising an annular rib received in an annular groove or a suction based closure means; Velcro® or similar.

Preferably, the seam is a welded seam, for example a heat welded seam.

Preferably, the sealing flap is hinged to the body of the ostomy bag along the line of the seam. This provides the advantage that the seam provides a hinge.

Preferably, the hinge is formed by a section of seam which is straight.

In use, when ballooning occurs, the user can discreetly remove the closure, gently squeeze the bag and release gas to return the bag to a comfortable size.

In other options, a valve might be used to close the exit aperture, the valve being easily activated by the user, for example by depressing or nipping an area around the aperture.

Figure 2:
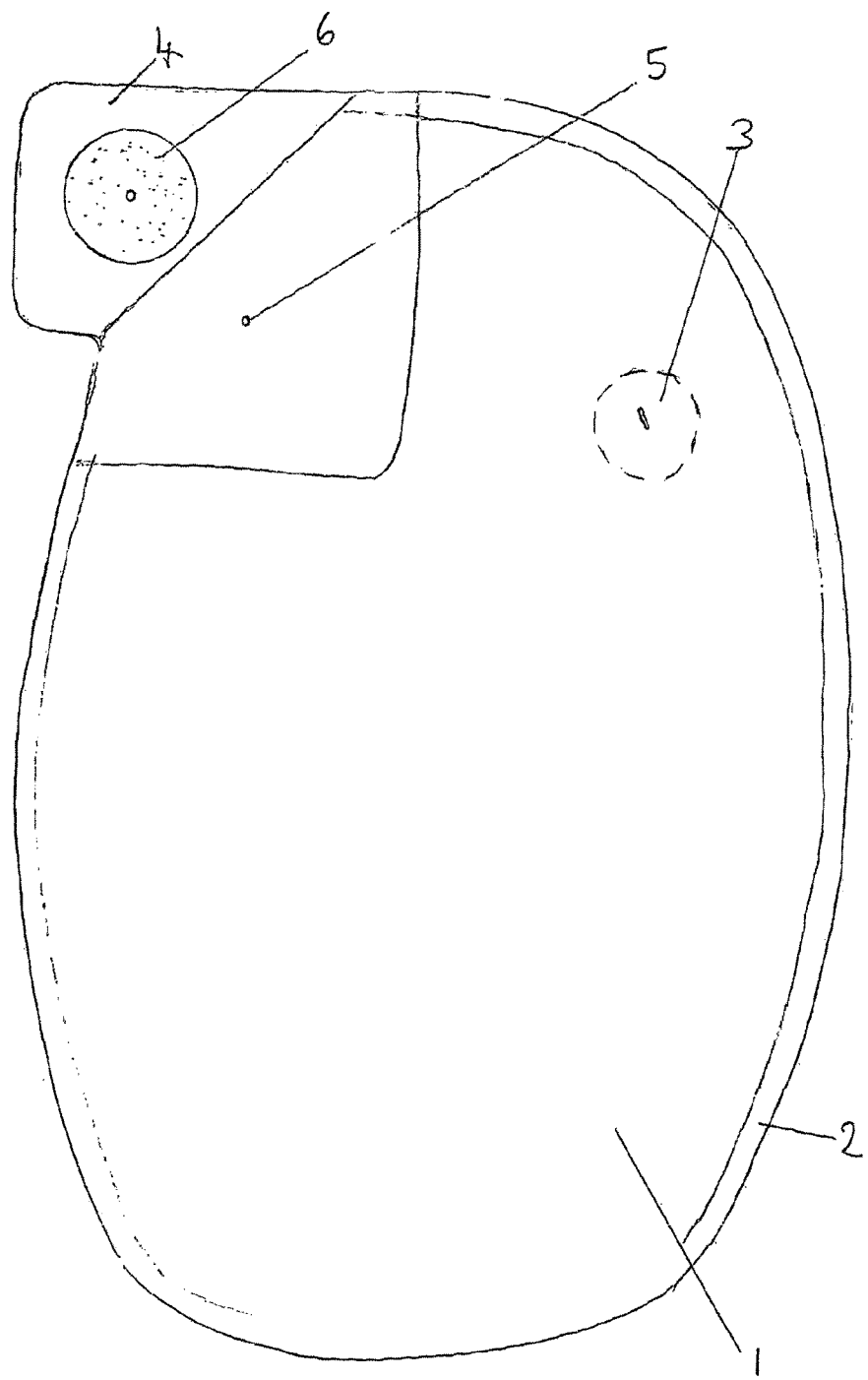

An embodiment of the invention will now be described with reference to the accompanying figures in which;

FIG. 1 shows a face on view of an embodiment of the invention with the exit aperture closed FIG. 2 shows a face on view of the embodiment of FIG. 1 with the exit aperture open FIG. 1 shows an external wall 1 of an ostomy bag which, in use, would face away from the user's skin and so is easily accessible to the user. A seam 2 around the periphery of the wall secures two walls together to form the bag. A filter 3 is located on the front of the wall for filtering odours and gradually releasing gaseous products from the bag.

In a corner of the wall 1 is a flap 4 which extends from the seamed region 2 and is folded onto the wall 1.

FIG. 2 shows the same embodiment with the flap 4 folded back away from the wall 1. This exposes an exit aperture 5 in the wall 1. On the under surface of the flap 4 can be seen a disc 6 which is covered in a reusable adhesive allowing the flap 4 to be repeatedly peeled away and re-secured to the wall 1 for the useful life of the bag.

In use, when the bag becomes inflated and uncomfortable, the user pulls back the flap 4 opening the exit aperture 5. By gently squeezing the bag excess gases can be quickly released and the aperture re sealed to prevent leakage of any remaining content in the bag.

I claim:

1. An ostomy bag comprising two walls which are joined together along a seam around the edge of the bag, one of said two walls being easily accessible to the user when the bag is in use as it will face away from the user's skin, the accessible wall including a closable exit aperture and a closure, which releasably covers the aperture for selectively releasing accumulated gas through the aperture, the closure being provided in the form of a sealing flap, which attaches to the bag by means of a reusable seal, and which folds down from a hinge formed along the line of the seam, the hinge being formed by a section of the seam which is substantially straight, the sealing flap being substantially triangular and wherein the hinge defines one edge of the triangle, the inner and outer pouch walls extending beyond the seam to provide the flap, including a portion of the inner wall and a portion of the outer wall of the pouch, wherein the flap comprises a disc which is covered by a reusable adhesive, such that the flap is configured to be repeatedly peeled away and re-secured to the outer wall of the pouch, thereby covering the exit aperture; wherein the flap and exit aperture are configured to release gas from the pouch when the flap is stored away from the exit aperture; and wherein the flap and exit aperture are configured to prevent the release of gas from the pouch when the flap is re-secured to the outer wall of the pouch.

2. An ostomy bag as claimed in claim 1 wherein the reusable seal comprises a peelable adhesive.

3. An ostomy bag as claimed in claim 1 wherein the reusable seal is a mechanical seal comprising an annular rib received in an annular groove.

4. An ostomy bag as claimed in claim 1 wherein the reusable seal uses suction.

* * * * *